US010327634B2

(12) United States Patent
Farberov

(10) Patent No.: US 10,327,634 B2
(45) Date of Patent: Jun. 25, 2019

(54) OPHTHALMIC LENS DOUBLET FOR OPHTHALMOSCOPY

(71) Applicant: Arkadiy Farberov, Newark, CA (US)

(72) Inventor: Arkadiy Farberov, Newark, CA (US)

( * ) Notice: Subject to any disclaimer, the term of this patent is extended or adjusted under 35 U.S.C. 154(b) by 0 days.

(21) Appl. No.: 15/699,469

(22) Filed: Sep. 8, 2017

(65) Prior Publication Data

US 2019/0076019 A1 Mar. 14, 2019

(51) Int. Cl.

| | |
|---|---|
| ***A61B 3/10*** | (2006.01) |
| ***A61B 3/12*** | (2006.01) |
| ***G02B 3/04*** | (2006.01) |
| *G02B 3/00* | (2006.01) |

(52) U.S. Cl.

CPC .............. *A61B 3/1208* (2013.01); *G02B 3/04* (2013.01); *G02B 2003/0093* (2013.01)

(58) Field of Classification Search

CPC ......... A61B 3/103; A61B 3/1015; A61B 3/12; A61B 3/112; A61B 3/107; A61B 3/1208; A61B 3/1025; A61B 3/102; G02B 3/04; G02B 2003/0093

USPC .......................................................... 351/205

See application file for complete search history.

(56) References Cited

U.S. PATENT DOCUMENTS

| | | | | |
|---|---|---|---|---|
| 4,627,694 A | | 12/1986 | Volk | |
| 4,738,521 A | | 4/1988 | Volk | |
| 5,046,036 A | | 9/1991 | Volk | |
| 5,333,017 A | | 7/1994 | Volk | |
| 5,523,810 A | * | 6/1996 | Volk | A61B 3/125 351/205 |

* cited by examiner

*Primary Examiner* — William R Alexander
*Assistant Examiner* — Henry A Duong

(57) ABSTRACT

Proposed is an ophthalmic lens doublet for indirect ophthalmoscopy. The doublet is cemented into an integral unit from two lens elements, of which is a convex-convex lens element and another is a convex-concave lens element. Both lens elements have external and internal surfaces and may be combined so that the ophthalmic lens doublet has asphericity either on one side or on both sides of the unit. The aspheric surface is characterized by asphericity Z of the following formula (1)

$$Z=Y^2/\{R+[R^2-(1+k)Y^2]^{1/2}\} \quad (1),$$

where Z is in one of coordinates in a Cartesian coordinate system, Y is a second coordinate in the Cartesian coordinate system, R and k being variable parameters which are different for each selected values of d, where d is an outer diameter of the ophthalmic lens doublet.

2 Claims, 2 Drawing Sheets

OPHTHALMIC LENS DOUBLET FOR OPHTHALMOSCOPY

FIELD OF THE INVENTION

The present invention relates to the field of ophthalmoscopy, in particular, to an ophthalmic lens doublet for indirect ophthalmoscopy used for observing the fundus and structure in the posterior chamber of a patient's eye.

BACKGROUND OF THE INVENTION

Ophthalmic lenses with light sources and dioptricity of 60 D and higher are known as Slit lamp lenses. Ophthalmic lenses with light sources and dioptricity of 40 D and lower are known as BIO lenses. They are used for indirect ophthalmoscopy with slit lamps or a light attached to a headband. In this case, a light source is a headlight, which is secured on the ophthalmologist's head, or a lamp that directs the light directly into the patient's eye via special mirror. The instruments that are used in the latter case are known as ophthalmoscopes.

Ophthalmoscopy is a test intended for observation of the fundus of the eye and other structures of the posterior chamber of an eye. The ophthalmoscopy is an eye examination procedure performed by an oculist as a part of a routine physical examination. It is important for determining the health of the retina, optic disc, vitreous humor, etc.

Prior Art section of U.S. Pat. No. 4,627,694 issued on December 1986 to David Volk describes the history of the ophthalmoscopy.

Single-piece lenses for observation of the posterior part of the vitreous cavity and the fundus of an eye were introduced into the ophthalmic practice in the 1950th.

First, conventional optical lenses with plano and spherical surfaces of various dioptric powers were used. Then, in 1956 and again in 1957 David Volk introduced so called conoid ophthalmic lenses. These conoid lenses were composed of one conoid surface and one spherical or plano surface, and also composed of two conoid surfaces. Later, such conoid ophthalmic lenses were used under the terms "aspherical lenses", "lenses with aspheric surfaces" generally accepted in optics. In the field of the ophthalmoscopy such lenses became known as Biolenses and Slit Lamp lenses.

An ophthalmic lenses of the type mentioned above differs from conventional optical lenses in that they are used in optical systems wherein an entrance pupil of the patient's eye plays a role of an optical lens and a diaphragm of a variable diameter.

Further development of ophthalmic lenses is presented in the number of patents granted to David Volk and Donald Volk.

In particular, U.S. Pat. No. 4,738,521 issued on Apr. 19, 1988 discloses a lens for use in indirect ophthalmoscopy. The lens has two functions: firstly, as a condensing lens converging light from an ophthalmoscope light source to the pupil of the eye and thereby illuminating the fundus of the eye, and secondly, as an image forming lens which forms an aerial image of the fundus of the eye, which is viewed monocularly with a monocular indirect ophthalmoscope or binocularly and stereoscopically with a binocular indirect ophthalmoscope. Both the front and back surfaces of the lens are positive aspheric surfaces of revolution of an aspheric type on a common axis of revolution, the dioptric power at the apex of the front surface of the lens being approximately twice that of the apex of the back surface of the lens, wherein the back surface faces the eye being examined. The eccentricity of the front surface has a definite relationship to the eccentricity of the back surface, the eccentricities of the two surfaces of the lens being a function of the sum of the dioptric powers of the two surfaces of the lens. The eccentricities and apical dioptric powers of the surfaces of the lens are such that the lens converges the light from the ophthalmoscope light source to a precise image of the source at the entrance pupil of the eye, and simultaneously the lens forms, with the light emerging from the eye, a substantially flat aerial image of the fundus of the eye in which images the aberrations of the image including curvature, astigmatism and distortion are optimally corrected.

U.S. Pat. No. 5,046,836 issued on Sep. 10, 1991 relates to a diagnostic indirect ophthalmoscopy contact lens system. A compound diagnostic indirect ophthalmoscopy contact lens described in this patent is intended for illumination and observation of the fundus of the eye. This two-lens assembly contains a plus powered meniscus aspheric contact element and a biconvex aspheric anterior element, each of the lens elements contributing positive refractive power to the optical system and co-acting to illuminate and form an aerial image of the fundus of the eye. For observation of the eye fundus, the device is brought into contact with the eye cornea. Such devices did not find wide application because of their relatively complicated use.

U.S. Pat. No. 5,333,017 issued on Jul. 26, 1996 discloses a lens specifically designed for use with a slit lamp biomicroscope in the examination of a patient's eye. One or more lens elements having first and second convex aspheric surfaces of revolution may be used. The first and second aspheric surfaces are coaxial and non-symmetrical with respect to one another. The aspheric surfaces are chosen to correct astigmatic imagery of the lens, with the formed aerial image free of excessive field curvature and astigmatism. The lens is held at a distance from the patient's eye pupil corresponding to the secondary focal length of the lens. If the examined eye is emmetropic and the lens is held in a position wherein the entrance pupil of the lens is conjugate with that of the examined eye, an image of the entrance pupil of the patient's eye will be formed at the pupil aperture of the optical system of the slit lamp biomicroscope used to observe the aerial image of the fundus as produced by the lens. The ratio of the apical radius of curvature of each surface and the ratio of the apical eccentricities of each surface are chosen to optimally correct for astigmatic imagery as well as the pupil imagery of the lens, being dependent upon the index of refraction of the optical quality glass or plastic used in the production of such lenses. The indirect ophthalmoscopy lens of the invention therefore provides a sharper, focused fundus image and a relatively wide field of view.

SUMMARY OF THE INVENTION

The present invention relates to the field of ophthalmoscopy, in particular, to lens doublet for indirect non-contact ophthalmoscopy used for observing the fundus and structure in the posterior chamber of a patient's eye.

The lens doublet of the invention is a hand-held ophthalmologic lens intended for the examination of a patient's eye by using a remote light source such as a slit lamp, or the like. The lens doublet consists of two optical lens elements which are cemented together into an integral body. One of these optical lens elements is an optical convex-convex lens element and the other one is an optical convex-concave lens element. The invention covers two modifications of the doublet, i.e., 1) a doublet with asphericity on one side and 2) a doublet with asphericity on both sides.

The convex-concave lens element and the convex-convex lens element of the doublet of the invention are coaxial with each other and are used for correction of astigmatism of the eye retina image and for forming an aerial image free of distortions caused by the curvature of the retina.

Formulas that describe the aforementioned aspheric surfaces include certain parameters the selection of which makes it possible to optimize asphericity for obtaining an image of the highest possible quality.

It was revealed that in the optical doublet of the invention the image quality of the object being observed depends mainly on glass refractive indices and refractive index ratios of the doublet lens elements. Other properties of the optical material of the lens elements such as a spectral dispersion, etc. also exerts a significant influence the image quality and have to be taken into account in design of the ophthalmic lens.

Conventionally, optical glasses used in doublets, e.g., in the objectives of microscopes or photo cameras, have greater differences in refractive indices than in the doublet of the invention. It has been found by the inventor that the use of doublets with glasses of component lens elements, even with small differences in refractive indices but with an unusually great difference in spectral dispersion, produces a noticeable synergistic effect manifested in significant improvement of the image quality. For example, resolution of the image (i.e., a number of lines per mm) can be doubled. In a conventional ophthalmic lens, resolution capacity in the field of view center (FOV center) is much higher than the resolution capacity in the periphery of the FOV (i.e., on the edge of the FOV) and the difference between both resolutions is significant. In the ophthalmic doublet of the invention this difference is much smaller. In addition, other properties such as brightness and contrast of the image are also noticeably improved as compared to a conventional ophthalmic lens.

In use, the lens doublet is held at a certain distance from the patient's eye pupil. corresponding to the distal focal length of the lens. The ophthalmic lens is held in a position wherein the entrance pupil of the lens is conjugate with that of the examined eye, and an image of the entrance pupil of the patient's eye will be formed at the pupil aperture of the optical system of a source of light, e.g., a slit lamp, or another light source which is used to observe the aerial image of the retina as produced by the lens.

DETAILED DESCRIPTION OF THE INVENTION

Figure 1:
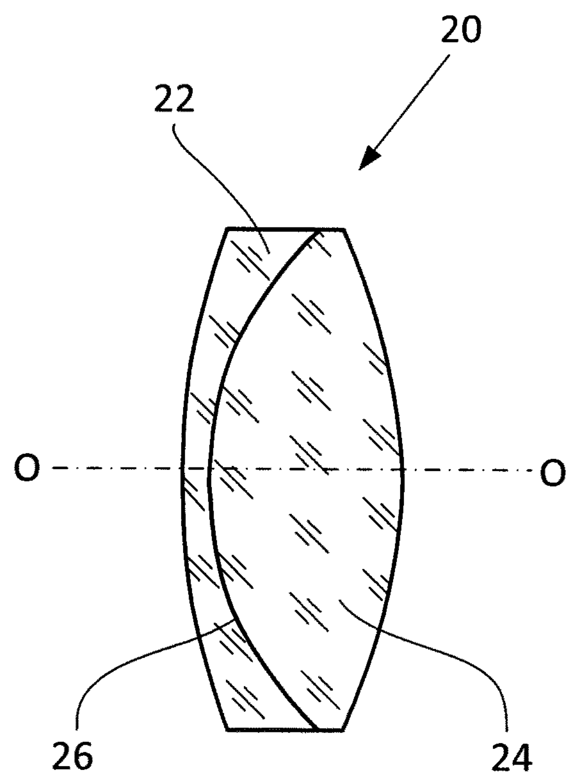
FIG. 1 is a cross-sectional view of the ophthalmic lens in a plane that contain the optical axis of the lens.

It is understood that because the size of the patient's retina image on the observer's retina is smaller than the illuminated area of the patient's retina, it seems it would be appropriate to make an ophthalmic lens with the diameter as big as possible. However, such an approach is associated with some problems. More specifically, a large field of view requires adequate image quality correction not only for the central field point but for edges as well. Usually, a conventional ophthalmic lens is a simple lens with spherical surfaces, and the above requirement leads to steep radii. It should be noted that the field of view depends not only on the lens diameter but rather on the focal or working distance of the ophthalmic lens, and the smaller is this distance, the higher is lens dioptricity and the greater the field of view.

Another reason for which lenses exclusively with spherical surfaces practically do not find use in ophthalmoscopy is that their geometric and chromatic aberration significantly distort imagery of the eye fundus of the patient observed by the ophthalmologist. Increasing the lens diameter leads to increase in thickness and weight of the lens. As has been mentioned earlier, this problem can be alleviated by making one of the lens surfaces aspherical. However, in order to simplify the lens and not to escalate its cost this aspherical surface was designed as a surface of a second order, which did not contribute much to the image quality of the edges of the field. Moreover, in such a design, it was still impossible to provide a good image performance at the edges of field of view, and resolution at these points was not enough to detect rather small retina defects.

The situation is even worse for higher optical power lenses with dioptricity of 50, 60 and 90. The field of views for these ophthalmic lenses are much wider and they require much more accurate viewer's eye positioning (see Tables 1 and 2 below).

That is why ophthalmologists prefer D20 lenses, and usually use higher optical power ones combining them with other optical devices.

In slit lamps with high dioptricity the field of view is much wider than in the case of slit lamps with smaller dioptricity. This is because the field of view depends on the focal distance of the lens. According to data of Volk and other manufacturers of similar products, the higher is dioptricity, the wider is the field of view. Nevertheless, increase in dioptricity leads to decrease in the lens diameter.

TABLE 1

| BIO Lens | | |
|---|---|---|
| Diopters | FOV (Field of View), deg. | F (Focal length), mm |
| 14D | 36 | 75 |
| 15D | 36 | 72 |
| 20D | 46 | 50 |
| 25D | 52 | 38 |
| 28D | 53 | 33 |
| 30D | 58 | 30 |
| 40D | 69 | 20 |

TABLE 2

| Slit Lamp | | |
|---|---|---|
| Diopters | FOV (Field of View), deg. | F (Focal length), mm |
| 90D | 74 | 7 |
| 90D | 95 (super FOV) | 7 |
| 90D | 103 (super super FOV) | 4-5 |
| 60D | 68 | 13 |

One of the significant shortcoming single lens loupes is presence of chromatic aberrations. These aberrations increase spot diagrams in image performance and significantly reduce resolution. In order to eliminate this problem cemented doublets are used for the loupe designs. With the combination of one aspherical surface they allow significant improvement of image performance and resolution for center and edges of the field.

The effect of the profile of the lens surface on the image quality can be compensated by introduction of asphericity on one or both surfaces of the lens (see, e.g., FIGS. 3, 4 and FIGS. 7 to 10 and associated descriptions of U.S. Pat. No. 5,333,017 issued to D. Volk on Jul. 26, 1994).

Nevertheless, the cemented ophthalmic lens doublets with at least one aspheric surface have enough room for further improvements.

The present invention relates to a structure of an ophthalmic lens made from materials with specific optical properties, wherein the lenses have one or two aspheric surfaces of specific geometry and ratios of optical parameters that allows almost to double resolution capacity of the ophthalmic lens.

More specifically, the lens doublet 20 is shown in FIG. 1 which is a hand-held ophthalmologic lens intended for the examination of a patient's eye by using a remote light source (not shown) such as a slit lamp, or the like. The lens doublet 20 consists of two optical lens elements 22 and 24, which are cemented together into an integral body along the interface surface 26 with the use of an optical cement (not shown). In the illustrated structure, optical lens element 22 is a convex-convex lens element and the other one, the lens element 24, is an optical convex-concave lens element.

The invention covers two modifications of the doublet, i.e., 1) a doublet with asphericity on one side of the doublet; and 2) a doublet with asphericity on both sides of the doublet. The convex-concave lens element and the convex-convex lens element of the doublet of the invention are coaxial with each other and are used for correction of astigmatism of the eye retina image and for forming an aerial image free of distortions.

Formulas that describe the aforementioned aspheric surfaces include certain parameters the selection of which makes it possible to optimize the asphericity for obtaining an image of the highest possible quality.

It was revealed that in the optical doublet of the invention the image quality of the object being observed depends mainly on refractive indices and refractive index ratios of the doublet lens elements. Other properties of the optical material of the lens elements such as a spectral dispersion, etc. also influence the image quality and have to be taken into account in design of the ophthalmic lens.

In use, the lens doublet is held at a certain distance from the patient's eye pupil. corresponding to the distal focal length of the lens. The ophthalmic lens is held in a position wherein the entrance pupil of the lens is conjugate with that of the examined eye, an image of the entrance pupil of the patient's eye will be formed at the pupil aperture of the optical system of a source of light, e.g., a slit lamp which is used to observe the aerial image of the retina as produced by the lens.

Each doublet of aforementioned Modifications 1) and 2) is considered separately in detail with respect to a 20 D lens for indirect ophthalmic observation of the patient eye. The 20 D lens is used as an example since the lenses of such dioptricity find the most frequent use in the art. It is understood that the application of the invention is not limited to the 20 D lenses and lenses of other dioptricities are also covered by the scope of the present invention. In general, dioptricity D may be selected in the range of 10 to 125 If a dioptricity of the ophthalmic lens doublet is beyond the aforementioned range, this will lead to the doublets with dimensions inconvenient for practical use. The ophthalmic lens doublet with D equal to or greater than 60 may find use in ophthalmic microscopes with slit lamps.

A Doublet with Asphericity on One Side, i.e., on the Outer Side of the Convex-Convex Lens Element with a First Set of Parameter (Modification 1)

Figure 2:
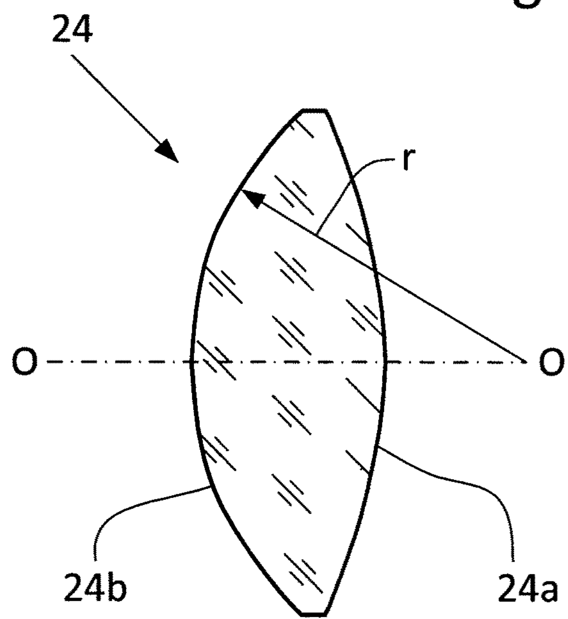
FIG. 2 is a cross-sectional view of the convex-convex lens element of the invention, which has the aspheric surface on the outer side facing the viewer and which has a first set of lens parameters.

The convex-convex lens element 24 of the double 20 that corresponds to the aforementioned Modification 1) is shown in FIG. 2. In the doublet of FIG. 1, the convex-convex lens element 24 has an outer convex surface 24*a* facing the viewer (not shown) and an inner spherical convex surface 24*b* which faces the second lens element 22 (FIG. 1) of the doublet 20. In this modification, the surface 24*a* is aspheric, and the surface 24*b* is spherical. The lens element 22 is a convex-concave lens element. It is understood that the lens elements 24 and 22 are cemented together into the structure of FIG. 1 with an optical cement (not shown). In this case, the cement affects neither optical properties of the doublet 20 nor quality of the image.

As mentioned above, both lens elements 22 and 24 are axisymmetric. Therefore, the aforementioned formula (1) describes a profile of the outer surface 24*a* of the lens element 24 in any cross-sectional plane that contains optical axis O-O of the lens 20.

In the modification of the lens element shown in FIG. 2, the outer diameter "d" of the lens element 24 ranges from 15 mm to 80 mm, and preferably is equal to 52 mm. The curvature radius r of the spherical surface 24*b* which is in contact with the convex-concave lens element 22 along the interface surface 26 ranges from 30 mm to 60 mm, and preferably is equal to 36 mm.

The asphericity Z, which is in one of the coordinates in the Cartesian coordinates Z, Y system, is defined by the following equation of the second order asphericity, which is the equation for all aspheric lenses:

$$Z=Y^2/\{R+[R^2-(1+k)Y^2]^{1/2}\} \quad (1),$$

where R and k are variable parameters which are different for each selected value of d, D, r, and refractive indices $n_1$ and $n_2$ of the optical material of lens elements 24 and 22, respectively. The refractive indices $n_1$ and $n_2$ of the material of lens elements 22 and 24 may be selected in the range of 1.510 to 1.810. In fact, for the illustrated design the inventor used optical glasses with refractive indices of 1.620 and 1.755.

As mentioned above, both lens elements 22 and 24 are axisymmetric. Therefore, the aforementioned formula (1) describes a profile of the outer surface 24*a* of the lens element 24 in any cross-sectional plane that contains optical axis O-O of the lens 20.

The best image quality can be achieved only with predetermined values of the parameters D, d, r, R, k, $n_1$, and $n_2$, which in this example are defined as the first set of lens parameters. It should be noted that the aforementioned parameters should be selected taking into account also such factors as spectral dispersions $Vd_1$ and $Vd_2$ of the optical materials of the lens elements 24 and 22.

For example, the following first set of lens parameters provides the best image quality at D=20: d=52 mm; r=36 mm; R=48.8±0.01 mm;

and k=−1.88±0.01; $n_1$=1.754, $n_2$=1.755; $Vd_1$=52.4, and $Vd_2$=27.4. Reference numeral r shown in FIG. 2 designates the radius on the spherical surface of the concave-concave lens element 24. In this example, r is equal to 36 mm.

In the illustrated example, the convex-concave lens element 22 (FIG. 1) is made from the optical material known as Schott Glass N-SF-4, and the convex-convex lens element 24 is made from Schott Glass—LAK 33.

It has been unexpectedly found that factor that produces the most noticeable influence on results of the image quality is the difference of spectral dispersities in lens elements 22 and 24.

A Doublet Wherein the Concave-Concave Lens Element has the Aspheric Surface on the Outer Side Facing the Viewer with the Second Set of Lens Parameter (Modification 1)

The following example is given herein to show that even an insignificant change in the geometry of the lens element (in this case the change of the radius Ron the spherical surface from R=36 mm to R=35 mm) drastically affects the asphericity parameters $k_1$ and $R_1$.

Figure 3:
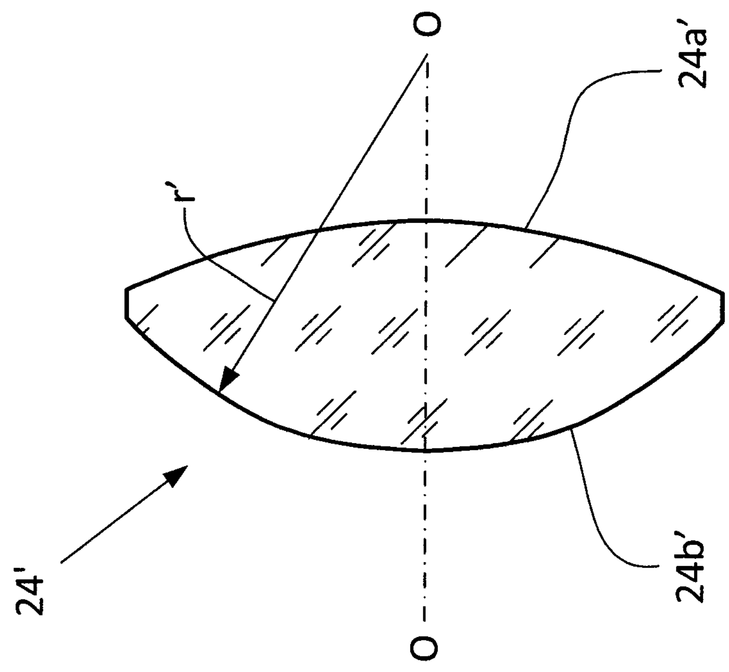
FIG. 3 is a cross-sectional view of the concave-concave lens element of the invention, which has the aspheric surface on the outer side facing the viewer and which has a second set of lens parameters.

Geometrically, the optical lens element shown in FIG. 3 with the second set of lens parameters has the same geometry as the optical lens of FIG. 2. The lens element of FIG. 3, which in its entity is designated by reference numeral 24' has an outer convex surface 24*a*' facing the viewer (not shown) and an inner convex surface 24*b*' which faces the second lens element 22 of the doublet (FIG. 1). In this modification, the surface 24*a*' is aspheric, and the surface 24*b*' is spherical. The lens element 22 is a convex-concave lens element, which may be the same as one shown in FIG. 1. It is understood that the lens elements 24' and 22" are cemented together into the structure of FIG. 1 with a conventional optical cement. In this case, the cement affects neither optical properties of the doublet 20 nor quality of the image.

As mentioned above, both lens elements 22 and 24' are axisymmetric. Therefore, the aforementioned formula (1), which is applicable also to the lens element of FIG. 3, describes a profile of the outer surface 24*a*' of the lens element 24' in any cross-sectional plane that contains optical axis O-O of the lens element 24'.

In the modification of the lens element shown in FIG. 3, the outer diameter d' of the lens element 24' ranges from 15 mm to 80 mm, and preferably is equal to 52 mm. The curvature radius r' of the spherical surface 24*b*' which is in contact with the convex-concave lens element 22 along the interface surface 26 and which is different from the respective radius r of the lens element of FIG. 2 is equal to 35 mm.

The asphericity Z', which is in one of the coordinates in the Cartesian coordinates Z, Y system, is defined by the same equation (1) of the second order asphericity, which is a standard equation for all aspheric lenses, where R and k are variable parameters which are different for each selected values of d, D, r', and refractive indices $n_1$ and $n_z$ of the optical material of lens elements 24' and 22, respectively.

As mentioned above, the best image quality can be achieved only with predetermined values of the parameters D, d, r', R, k, $n_1$, and $n_2$. It should be noted that the aforementioned parameters should be selected taking into account also such factors as spectral dispersions $Vd_1$ and $Vd_2$ of the optical materials of the lens elements 24' and 22.

For example, in this example the following parameters correspond to D=20: d=52 mm; r'=35 mm; R=40.0±0.1 mm; and k=−2.14±0.02; n1=1.620, n2=1.620; Vd1=38.1, and Vd2=60.3. Reference numeral r' shown in FIG. 3 designates the +radius of the spherical surface of the convex-convex lens element 24' and on the concave surface of the lens element 22 and is equal to r'=35 mm.

In the illustrated example, the convex-concave lens element 22 is made from the optical material known as OHARA PBM-9, and the convex-convex lens element 24' is made from Schott Glass—SK 16.

The example of the ophthalmic lens of FIG. 1 with the use of the convex-convex lens element 24' also confirmed the unexpected synergic effect of the spectral dispersities in lens elements 22 and 24 on the quality of the image observed by the viewer.

A Doublet of Item 2) with Asphericity on Both Sides of the Doublet

Figure 4:
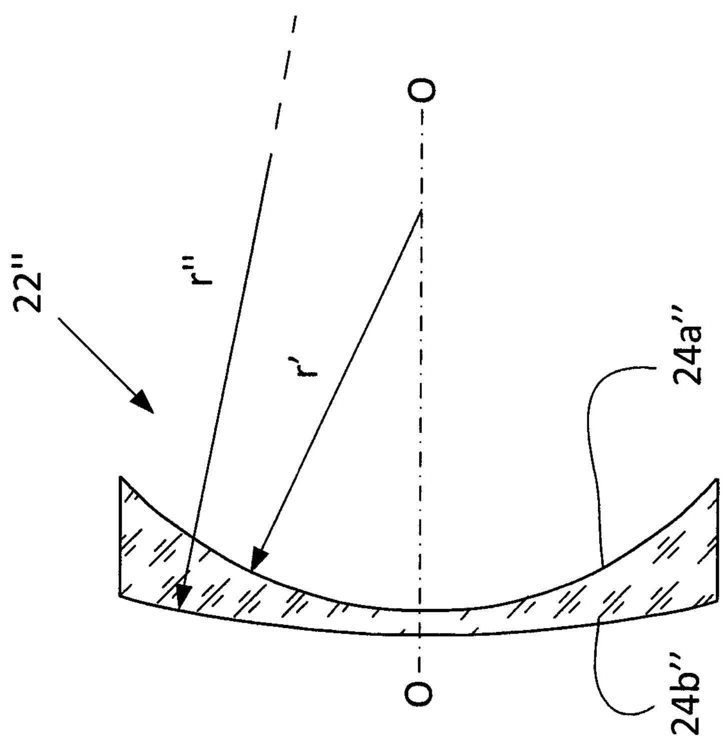
FIG. 4 is a convex-concave lens element of the doublet of the invention.

A convex-concave lens element 22" of the doublet of Item 2) is shown in FIG. 4 in a cross-section of the lens 20 by a plane that contains optical axis O-O of the lens 20. The lens element 22" has an internal concave surface 24*a*", which is spherical and an external convex surface 24*b*", and an external surface 24*b*" which is aspheric.

In its shape, the optical lens element 22" shown in FIG. 4 is the same as the optical element 22 of FIG. 1.

It is understood that the lens elements 22" is to be cemented together to a respective convex-convex lens element such as the lens element 24' of FIG. 3 to form the integral ophthalmic lens 20 of FIG. 1. Both elements are cemented together with the same optical cement as indicated above. In this case, the cement affects neither optical properties of the doublet 20 nor quality of the image.

As mentioned above, both lens elements 22" and the mating convex-convex lens element 24 or 24' are axisymmetric. Therefore, the aforementioned equation (1), which is applicable also to the lens element of FIG. 4, describes a profile of the aspherical convex surface 24*b*".

In the modification of the lens element 22" shown in FIG. 4, the outer diameter d" (not shown) of the lens element 22" ranges from 15 mm to 80 mm, and preferably is equal to 52 mm. The curvature radius r' of the inner, i.e., the spherical surface 24*a*" which is in contact with the convex-convex lens element 24 or 24', along the interface surface 26 (FIG. 1) is equal to 35 mm.

The asphericity Z, which is in one of the coordinates in the Cartesian coordinates Z, Y system, is defined by the above equation (1) of the second order asphericity, where parameters R and k will be different for lens elements 22" with different values r' of the radius on the spherical surface.

Thus, it has been shown that depending on whether the ophthalmic lens doublet has aspheric surface(s) on one or both external sides, the ophthalmic lens doublet of the invention may be either a single-asphericity ophthalmic lens doublet or a double-asphericity ophthalmic lens doublet.

As mentioned above, the best image quality can be achieved only with predetermined values of the parameters D, d, r', R, k, $n_1$, and $n_2$. It should be noted that the aforementioned parameters should be selected also taking into account such factors as spectral dispersions $Vd_1$ and $Vd_2$ of the optical materials of the lens elements 24' and 22.

For example, in this modification the following parameters correspond to D=20: d=52 mm; r'=35 mm; R=75±0.1; and k=1.1±0.01; n1=1.805, n2=1.697; Vd1=25.4, and Vd2=55.4.

In the illustrated example, the convex-concave lens element 22" is made from the optical material known as Schott Glass N-SF-6, and the convex-convex lens element 24' is made from Schott Glass—N-LAK 14.

In use, the lens doublet is held at a certain distance from the patient's eye pupil, corresponding to the distal focal length of the lens. The ophthalmic lens is held in a position wherein the entrance pupil of the lens is conjugate with that of the examined eye, an image of the entrance pupil of the patient's eye will be formed at the pupil aperture of the optical system of a source of light, e.g., a slit lamp which is used to observe the aerial image of the retina as produced by the lens.

The following table illustrates advantages of the ophthalmic lens doublet of the invention over conventional ophthalmic lens doublet of the same class. The comparison relates to optical characteristics of ophthalmic lens having 20 D dioptricity with practically equal fields of view (FOV).

In the following Table 3, the single-asphericity lens doublet and the double-asphericity lens doublet are characterized by fields of views in terms of degrees, image magnification in terms of magnification rate, a resolution capacity in terms of lines per mm in the center of the field-of view, and a peripheral resolution capacity in terms of lines per mm.

Other examples of optical glasses and their characteristic suitable for realization of the doublets of the present invention are shown in Table 3.

TABLE 3

| |
|---|
| Example 1<br>Doublet No. 1 |
| Concave-Convex Lens: aspheric; Schott Glass: N-SF6,<br>glass code: 1.805 254<br>$n_1 = 1.805$; $Vd_1 = 25.4$<br>Convex-Convex Lens: aspheric; Schott Glass: N-LAK14,<br>glass code: 1.697 554;<br>$n_2 = 1.697$; $Vd_1 = 55.4$<br>Magnification rate: 2.0 to 3.30<br>Example 2<br>Doublet No. 2 |
| Concave-Convex Lens: spherical; Glass: OHARA PBM 9,<br>glass code: 1.620 381;<br>$n_1 = 1.620$; $Vd_1 = 38.1$<br>Convex-Convex Lens: aspheric; Schott Glass: SK 16,<br>glass code: 1.620 603;<br>$n_2 = 1.620$; $Vd_1 = 60.3$<br>Magnification rate: 2.0 to 3.30<br>Example 3<br>Doublet No. 3 |
| Concave-Convex Lens: spherical; Schott Glass: S-SF 4,<br>glass code: 1.755 276;<br>$n_1 = 1.755$; $Vd_1 = 27.6$<br>Convex-Convex Lens: aspheric; Schott Glass: N-LAK 33,<br>glass code: 1.755 523;<br>$n_2 = 1.755$; $Vd_1 = 52.3$<br>Magnification rate: 2.0 to 3.30 |

It has also been revealed that the use of doublets with glasses of composite lens elements of the invention even with small differences in refractive indices but with an unusually great difference in spectral dispersion produces a noticeable synergistic effect manifested in significant improvement of the image quality. For example, the resolution capacity of the image can be doubled (see Table 4 below).

TABLE 4

| Model for 20 D | Materials | Field of View (FOV), deg. | Magnification rate | Resolution capacity in the FOV Center (lines/mm) | Peripheral (18 deg) Resolution capacity (lines/mm) |
|---|---|---|---|---|---|
| Single-asphericity lens | Schott Glass BK7 1.517 642 | 46 | 3.13x | 72 | 2 |
| Double-asphericity lens doublet | Schott Glass N-SF-6 1.805 254 N-LAK 14 1.697 554 | 46 | 3.13x | 132 | 18 |
| Single-asphericity lens doublet | Schott Glass K 9 1.620 383 SK 16 1.620 603 | 46 | 3.13x | 185 | 18 |
| Single-asphericity lens doublet | Schott Glass N-SF-4 1.755 276 LAK 33 1.755 523 | 48 | 3.13x | 190 | 19 |

Thus, it has been found that the use of doublets with glasses of component lens elements, even with small differences in refractive indices but with an unusually great difference in spectral dispersion, produces a noticeable synergistic effect manifested in significant improvement of the image quality. For example, the number of lines per mm can be doubled.

For example, a conventional single-aspherity lens of 20 D made from Schott Glass BK7 1.517 642 with a FOV of 46° and magnification rate of provides resolution capacity in the FOV Center equal to 72 lines/mm and peripheral (18° to normal direction) resolution capacity of 2 lines/mm. In contrast to this, the doublets of the invention cemented from the lens elements shown in Table 4 made it possible to provide resolution capacities in the FOV center in the range of 132 to 190, and the peripheral resolution capacity in the range of 18 to 19 lines/mm. It can be seen that the resolution capacity of the ophthalmic lens was more than doubled.

Although the invention has been described and illustrated with reference to specific examples of the ophthalmic lens doublets, it is understood that the invention is not limited by the illustrated examples and that any changes and modifications which do not depart from the scope of the attached patent claims are possible. For example, the lenses can be made from other optical materials with appropriate optical properties. The same principle is applicable for lens elements with dioptricities different from D20 and may have dioptricities smaller or greater than D20, etc.

What I claim is:

1. An ophthalmic lens doublet which has dioptricity D and is intended for indirect ophthalmoscopy, the ophthalmic lens doublet comprising:

a first lens element, which is a convex-concave lens element, and a second lens element, which is a convex-convex, wherein both have external surfaces and internal surfaces and are cemented together into a single ophthalmic lens doublet over their internal surfaces, one of the external surfaces of the ophthalmic lens doublet being an aspheric surface and the other external surface being selected from a spherical surface and an aspheric surface, so that the ophthalmic lens doublet may comprise a single aspheric surface doublet or a two aspheric surface doublet, the aspheric surface being characterized by an asphericity Z of the following formula (1)

$$Z=Y^2/\{R+[R^2-(1+k)Y^2]^{1/2}\} \quad (1),$$

where Z is in one of coordinates in a Cartesian coordinate system, Y is a second coordinate in the Cartesian coordinate system, a spherical surface radius R and a conic constant k being variable parameters which are different for each selected values of d, where d is an outer diameter of the ophthalmic lens doublet, the first lens element being made from a first optical material and the second lens element is made from a second optical element, and wherein the first lens element is made from the first optical material and the second optical element is made from a second optical material have different optical dispersions, wherein a curvature radius r of the spherical surface on the inner surface of the first optical lens element ranges from 30 mm to 60 mm.

2. An ophthalmic lens doublet which has dioptricity D and is intended for indirect ophthalmoscopy, the ophthalmic lens doublet comprising:

a first lens element, which is a convex-concave lens element, and a second lens element, which is a convex-convex, wherein both have external surfaces and internal surfaces and are cemented together into a single ophthalmic lens doublet over their internal surfaces, one of the external surfaces of the ophthalmic lens doublet being an aspheric surface and the other external surface being selected from a spherical surface and an aspheric surface, so that the ophthalmic lens doublet may comprise a single aspheric surface doublet or a two aspheric surface doublet, the aspheric surface being characterized by an asphericity Z of the following formula (1)

$$Z=Y^2/\{R+[R^2-(1+k)Y^2]^{1/2}\} \quad (1),$$

where Z is in one of coordinates in a Cartesian coordinate system, Y is a second coordinate in the Cartesian coordinate system, R and k being variable parameters which are different for each selected values of d, where d is an outer diameter of the ophthalmic lens doublet, the first lens element being made from a first optical material and the second lens element is made from a second optical element, and wherein the first lens element is made from the first optical material and the second optical element is made from a second optical material have different optical dispersions, wherein the single-asphericity lens doublet and the double-asphericity lens doublet are characterized by fields of view in terms of degrees, image magnification in terms of magnification rate, a resolution capacity in terms of lines per mm in the center of the field-of view, and a peripheral resolution capacity in terms of lines per mm, and wherein the field of view ranges from 46 to 48, the magnification rate is equal to 3.13×, the resolution capacity in the center of the field-of view ranges from 180 to 190, and the peripheral resolution capacity ranges from 12 to 18, and wherein the first optical material has a spectral dispersion $Vd_1$, the second optical material has a spectral dispersion $Vd_2$, wherein a spectral dispersion ratio $Vd_1/Vd_2$ is selected in a range of 1.5 to 2.5, and wherein the resolution capacity provided by the doublet ranges from 132 to 190 lines/mm.

* * * * *